United States Patent [19]

Satake

[11] Patent Number: 5,148,808

[45] Date of Patent: Sep. 22, 1992

[54] ULTRASONIC DIAGNOSTIC APPARATUS DETECTING DOPPLER SHIFT

[75] Inventor: Nozomi Satake, Nishinasunomachi, Japan

[73] Assignee: Kabushiki Kaisha Toshiba, Kawasaki, Japan

[21] Appl. No.: 529,438

[22] Filed: May 25, 1990

[30] Foreign Application Priority Data

May 29, 1989 [JP] Japan ................................ 1-135509

[51] Int. Cl.$^5$ .............................................. A61B 8/06
[52] U.S. Cl. .......................... 128/660.05; 128/661.09
[58] Field of Search ............ 128/660.05, 660.07–661.1; 73/861.25

[56] References Cited

U.S. PATENT DOCUMENTS

| | | | |
|---|---|---|---|
| 4,217,909 | 8/1980 | Papadofrangakis et al. | 128/660.05 |
| 4,888,694 | 12/1989 | Chesarek | 364/413.24 |
| 4,915,115 | 4/1990 | Sasaki et al. | 228/660.05 |
| 4,918,605 | 4/1940 | Shirasaka | 128/660.05 X |
| 4,972,838 | 11/1990 | Yamazaki | 128/660.05 X |
| 4,993,417 | 2/1991 | Seo | 128/661.09 |
| 5,014,710 | 5/1991 | Maslak et al. | 128/660.05 |

FOREIGN PATENT DOCUMENTS 64-43237 2/1989 Japan .

*Primary Examiner*—Francis Jaworski
*Attorney, Agent, or Firm*—Oblon, Spivak, McClelland, Maier & Neustadt

[57] ABSTRACT

By transmitting ultrasonic waves along a section of an object under examination, brightness modulating reflected ultrasonic waves from respective points in the section to obtain a B-mode tomography image, and displaying Doppler shifted frequencies of the reflected ultrasonic waves from the respective points in the tomography image in colors, a Doppler flow mapping image indicating blood flow two-dimensionally can be obtained. Also, by transmitting ultrasonic waves many times only in the direction of a desired observation point and analyzing the spectrum of Doppler shifted frequencies of reflected ultrasonic waves from the observation point, a blood flow pattern waveform indicating time-varying blood flow velocity can be obtained. In an ultrasonic diagnostic apparatus which transmits ultrasonic waves repeatedly to a subject under examination at regular intervals and detecting Doppler shifts of reflected ultrasonic waves to obtain the Doppler flow mapping image and the blood flow pattern waveform, by transmitting ultrasonic waves alternately in the direction needed to prepare the Doppler flow mapping image and in the direction needed to prepare the blood flow pattern waveform at each time of transmission of ultrasonic waves, the Doppler flow mapping image and the blood flow pattern waveform can be displayed simultaneously while improving detectable low velocity in the Doppler flow mapping image without degrading aliasing velocity in the blood flow pattern waveform.

11 Claims, 5 Drawing Sheets

| MODE | | SCANNING ORDER OF RASTERS | BDF fd min | BDF fd max | FFT fd max |
|---|---|---|---|---|---|
| BDF | 1 | B₁ B₁ B₁ ⋯ B₂ B₂ B₂ ⋯ | $\pm\frac{fr}{8}$ | $\pm\frac{fr}{2}$ | — |
| | 2 | B₁ B₂ B₁ B₂ B₁ ⋯ B₃ B₄ B₃ B₄ ⋯ | $\pm\frac{fr}{16}$ | $\pm\frac{fr}{4}$ | — |
| | 3 | B₁ B₂ B₃ B₁ B₂ B₃ B₁ ⋯ B₄ B₅ B₆ B₄ B₅ ⋯ | $\pm\frac{fr}{24}$ | $\pm\frac{fr}{6}$ | — |
| BDF/ FFT | 1 | B₁ D B₁ D B₁ D ⋯ B₂ D B₂ D B₂ ⋯ | $\pm\frac{fr}{16}$ | $\pm\frac{fr}{4}$ | $\pm\frac{fr}{4}$ |
| | 2 | B₁ B₂ D B₁ B₂ D ⋯ B₂ D B₃ D B₄ D B₃ ⋯ | $\pm\frac{fr}{32}$ | $\pm\frac{fr}{8}$ | $\pm\frac{fr}{4}$ |
| | 2a | B₁ B₂ D B₂ D B₁ D ⋯ B₃ B₄ D B₄ D B₃ ⋯ | $\pm\frac{fr}{24}$ | $\pm\frac{fr}{6}$ | $\pm\frac{fr}{6}$ |
| | 3 | B₁ D B₂ D B₁ D B₂ ⋯ B₄ D B₅ ⋯ | $\pm\frac{fr}{48}$ | $\pm\frac{fr}{12}$ | $\pm\frac{fr}{4}$ |
| | 3a | B₁ B₂ B₃ D B₁ B₂ B₃ D ⋯ B₄ B₅ B₆ D ⋯ | $\pm\frac{fr}{32}$ | $\pm\frac{fr}{8}$ | $\pm\frac{fr}{8}$ |

F I G. 6

ULTRASONIC DIAGNOSTIC APPARATUS DETECTING DOPPLER SHIFT

BACKGROUND OF THE INVENTION

1. Field of the Invention

The present invention relates to an ultrasonic diagnostic apparatus which irradiates blood flow with ultrasonic waves and detects frequency shifts (Doppler shifts) of reflected ultrasonic waves from the blood flow to detect the flow direction and velocity.

A type of such ultrasonic diagnostic apparatus is a Doppler flow mapping apparatus for displaying a blood flow image contained within a monochrome tomography image (B mode image) in colors according to its direction and velocity, or more accurately, a B-mode blood flow imaging (referred to as BDF) apparatus. In general, the blood flow in the direction of a piezoelectric transducer is displayed in a red color, the blood flow in the direction opposite to the transducer is displayed in a blue color and the turbulent flow is displayed in a green color. The blood flow velocity is displayed in brightness. With such a BDF apparatus, abnormalities of the blood flow, such as regurgitation, stricture and shunt blood flow, can be observed in real time. However, the decision whether the blood flow is either in an artery or in a vein or the more detailed inspection such as detection of the absolute value of the blood flow velocity or the extent of the stricture cannot be made. For a detailed inspection, therefore, a spectrum analyzer has been developed which analyzes the frequency spectrum of Doppler shifted reflected waves. In general, as a spectrum analyzing method, a fast Fourier transform (FFT) method which is high in calculation precision is used. The result of the fast Fourier transform is displayed as a blood flow pattern waveform in which the axis of ordinate represents flow velocity and the axis of abscissa represents time. From the pattern waveform the absolute value of and variations with time in the flow velocity can be recognized.

Conventionally the B-mode blood flow imaging apparatus and the frequency analyzer have been independent of each other. Even if they are installed within the same apparatus, they are independent of each other in mode of operation. This is because the direction of transmission of an ultrasonic wave has to be changed at each irradiation in the BDF apparatus or in the BDF mode for obtaining a tomography image, while the direction of ultrasonic-wave transmission is fixed in the FFT apparatus or the FFT mode for obtaining variations in the flow velocity with respect to time at a certain point. Even with a conventional apparatus provided with the two modes of operation, therefore, the position and direction of the blood flow are identified in the BDF mode to determine a desired observation point for the FFT and the operation is then switched to the FFT mode so that the direction of transmission of ultrasonic waves is fixed to the direction of the observation point, a reflection signal from the observation point is range gated to obtain a reflection signal arising from the observation point only and Doppler shifts obtained from the reflection signal are fast Fourier transformed to display a blood flow pattern waveform. In order to observe the blood flow pattern waveforms at several points, therefore, the operation mode has to be switched many times between the BDF mode and the FFT mode, thus providing poor operability and taking a long time to make diagnostic. Furthermore, the detectable maximum value of the Doppler frequencies corresponds to half the repetition frequency (rate frequency) of transmission of ultrasonic waves and thus the part of the waveform above the maximum value will be turned down to the opposite polarity side of the waveform.

SUMMARY OF THE INVENTION

It is therefore an object of the present invention to provide an ultrasonic diagnostic apparatus which permits a blood flow image by the Doppler flow mapping and a blood flow pattern waveform by frequency spectrum analysis to be obtained substantially in real time.

It is another object of the present invention to provide an ultrasonic diagnostic apparatus which permits the measurable lower limit velocity of the blood flow in Doppler flow mapping to be lowered without the occurrence of aliasing of a blood flow pattern waveform and thus permits a high-resolution blood flow image and a blood flow pattern waveform which is low in deterioration due to the waveform aliasing to be displayed substantially in real time.

An ultrasonic diagnostic apparatus of the present invention comprises means for scanning a section of an object under examination with ultrasonic waves to obtain a tomography image of the object, means for detecting Doppler shifts of the reflected ultrasonic waves from many points in the slice, Doppler flow mapping means for displaying blood flow in colors in the tomography image according to the detected Doppler shifts to obtain a blood flow image, spectrum analyzing means for analyzing the frequency spectrum of Doppler shifts of reflected ultrasonic waves from a given point in the tomography image to obtain a blood flow pattern indicating time-varying flow velocity, means for displaying the blood flow image obtained by the Doppler flow mapping means and the blood flow pattern obtained by the spectrum analyzing means, and means for setting the direction of transmission of ultrasonic waves to the direction required by the Doppler flow mapping means or the direction required by spectrum analyzing means in a fixed order.

According to the ultrasonic diagnostic apparatus of the present invention, the blood flow image by the Doppler flow mapping and the blood flow pattern by the spectrum analysis can be obtained substantially in real time. Furthermore, the direction of transmission of ultrasonic waves for the Doppler flow mapping is cyclically changed in several consecutive directions in a predetermined number of times so that the lower limit of detectable flow velocity of the blood flow image can be lowered without lowering the aliasing velocity of the blood flow pattern. Therefore, a high-resolution blood flow image and a blood flow pattern which is low in degradation due to the aliasing can be displayed substantially in real time.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention and, together with the general description given above and the detailed description of the preferred embodiments given below, serve to explain the principles of the invention.

FIG. 6 illustrates scanning order in rasters and detectable Doppler shifted frequency ranges in the BDF mode and the FFT mode in all the embodiments of the present invention.

DETAILED DESCRIPTION OF THE PREFERRED EMBODIMENTS

Figure 1:
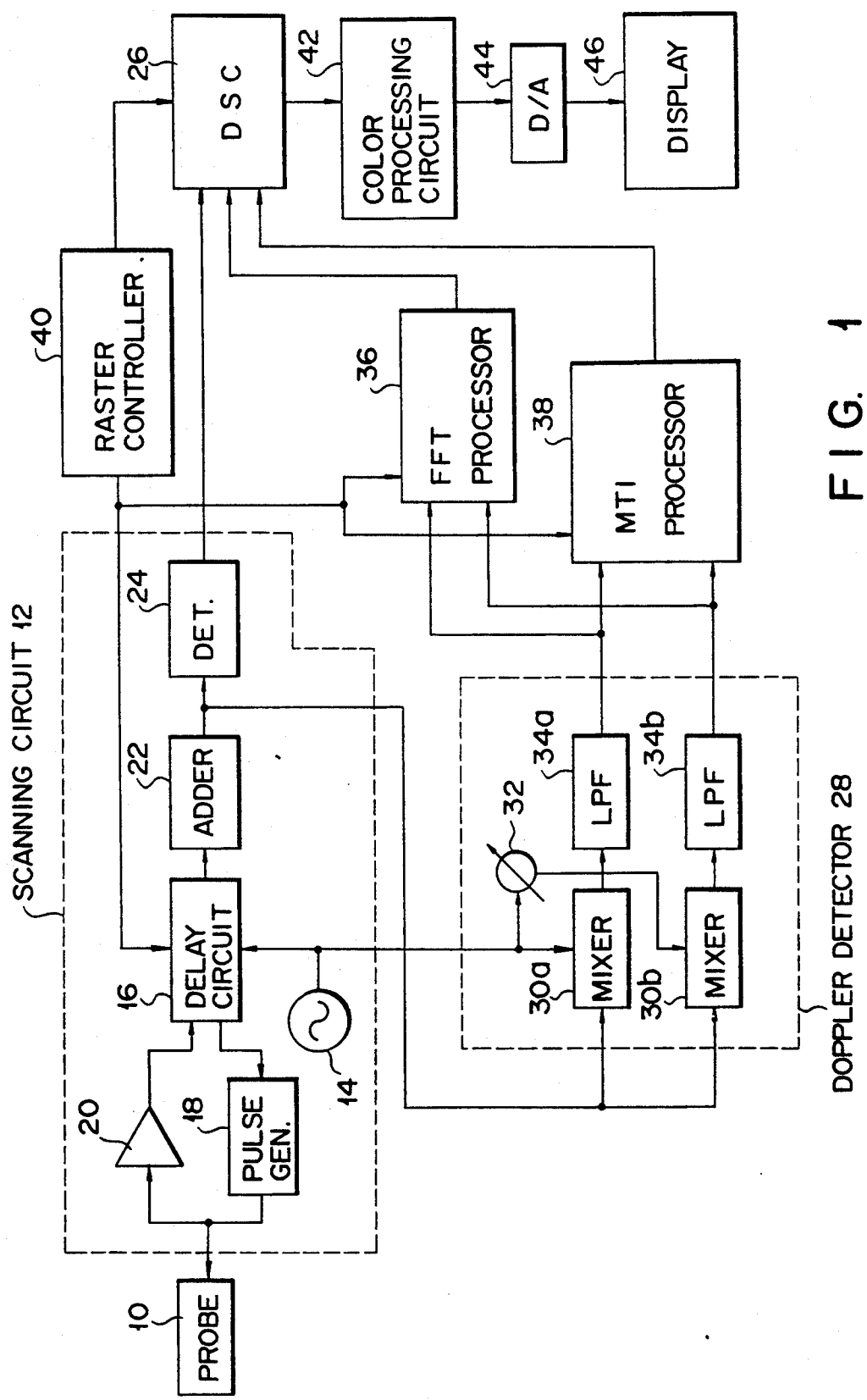
FIG. 1 is a block diagram of an ultrasonic diagnostic apparatus according to a first embodiment of the present invention.

An ultrasonic diagnostic apparatus according to a preferred embodiment of the present invention will be described with reference to the accompanying drawings. In FIG. 1, a scanning circuit 12 is connected to an electronic sector scanning type ultrasonic probe 10. Probe 10 comprises a large number of piezoelectric transducers arrayed in a row. By varying the timing of applying of voltages to the respective transducers, it is possible to cause ultrasonic waves to scan a sector or focus the ultrasonic waves. The probe 10 needs not be limited to the electronic sector scanning type and it may be of a linear scanning type or a mechanical scanning type. In scanning circuit 12, an output of an oscillator 14, which determines an oscillation frequency of the ultrasonic transducers, is applied to probe 10 via a delay circuit 16 and a pulse generator 18. Pulse generator 18 periodically supplies probe 10 with driving pulses. The inverse of the period is the repetition frequency (rate frequency) of the ultrasonic waves. Delay circuit 16 comprises a large number of delay lines having variable delay times. The outputs of the delay lines are coupled to the respective transducers. By varying the delay times, it becomes possible to vary the directions (raster directions) of the ultrasonic waves transmitted from probe 10. The delay times are controlled by control signals from a raster controller 40.

An output signal of probe 10 is applied to an adder 22 via a preamplifier 20 and delay circuit 16. In this case as well, output signals of the transducers are applied to adder 22 via corresponding delay lines after the same delays as those at the time of transmission. An output signal of adder 22 is applied to a detector 24 to detect the intensity of a reflection of the ultrasonic wave in each of the raster directions. An output of adder 24 is applied to a digital scan converter (DSC) as brightness information in each of the raster directions, that is, B-mode image (tomography image) information. The raster scanned by ultrasonic probe 10 is of a sector form and the raster of a display 46 is scanned horizontally as in the standard television system. DSC 26 adapts an input image to the standard television system by changing the scanning direction.

Output signals of adder 22 and oscillator 14 are also applied to a Doppler detector 28, which detects Doppler shifted frequencies and comprises mixers 30a and 30b, a 90° phase shifter 32 and low-pass filters (LPF) 34a and 34b. The output signal of adder 22 is multiplied by the output signal of oscillator 14 in mixer 30a and by the 90° phase shifted output signal of oscillator 14 from phase shifter 32 in mixer 30b. For this reason, Doppler shifted frequencies and high frequency components (Doppler shifted frequencies and double the transmission frequency) are obtained from mixers 30a and 30b. LPFs 34a and 34b remove high frequency components from the output signals of mixers 30a and 30b to provide cosine components and sine components of the Doppler shifted frequencies, respectively. The reason why the Doppler shifted frequencies contain cosine and sine components is to detect the polarity of the Doppler shifts.

Output signals of LPFs 34a and 34b are applied to an FFT (fast Fourier transform) processor 36 for frequency analysis and to an MTI (moving target indicator) processor 38 for color Doppler mapping. Output signals of processors 36 and 38 are also applied to DSC 26. FFT processor 36 and MTI processor 38 are also supplied with raster control signals from raster controller 40.

An output signal of DSC 26 is applied to a display 46 via a color processing circuit 42 and a D/A converter 44. Although not shown, the output signal of D/A converter 44 may be applied to a recorder such as video tape recorder.

Figure 2:
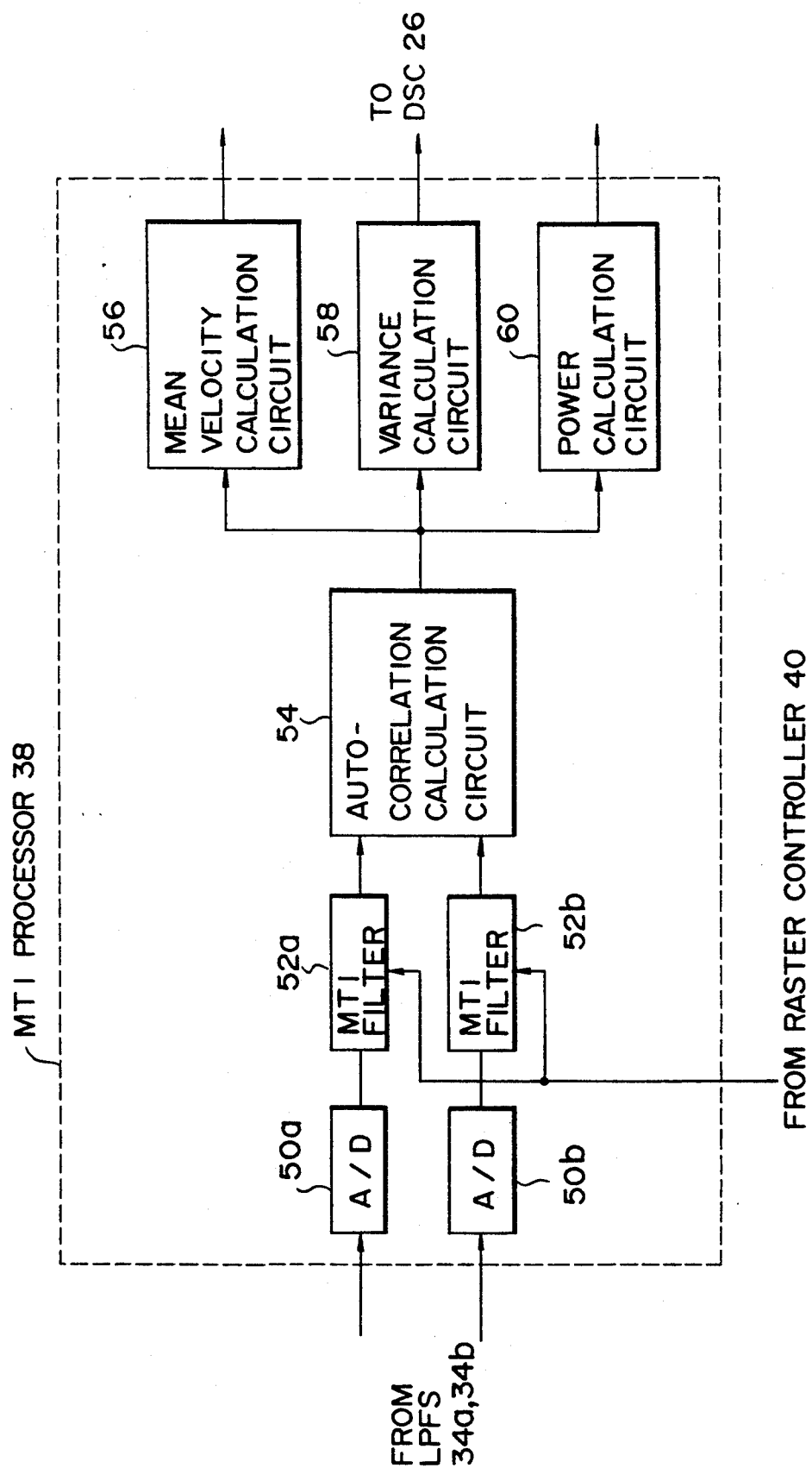
FIG. 2 is a detailed block diagram of the MTI processor of FIG. 1.

FIG. 2 is a detailed block diagram of MTI processor 38. The output signals of LPFs 34a and 34b are applied to an auto-correlation calculation circuit 54 via A/D converters 50a and 50b and MTI filters 52a and 52b. An output signal of auto-correlation calculation circuit 54 is applied to a mean velocity calculation circuit 56, a variance calculation circuit 58 and a power calculation circuit 60. Output signals of calculation circuits 56, 58 and 60 are applied to DSC 26. MT filters 52a and 52b are adapted to remove unwanted reflected components (clutter components) from fixed reflecting tissues (blood vessel walls, heart walls and so on) and comprises a digital filter of low-pass characteristics. The timing of sampling in the digital filter is controlled by the raster control signal. This is required because the BDF mode and the FFT mode are mixed in the present embodiment and the sampling timing should be synchronized with the raster control. Alternatively, the MTI filter may be comprised of a delay line and a subtracter so as to remove a clutter component by subtracting a reflected signal of a given time after from each reflected signal on an analog basis. Output signals of mean velocity calculating circuit 56, variance calculating circuit 58 and power calculating circuit 60 are applied to DSC 26. In color processing circuit 42, the blood flow coming near the probe is indicated by a red color, the blood flow leaving the probe is indicated by a blue color, the mean velocity of the blood flow is indicated by the brightness of a color and the velocity variance is indicated by a hue (mixed with green) as in the prior art. A resulting color Doppler image is displayed on display 46.

Figure 3:
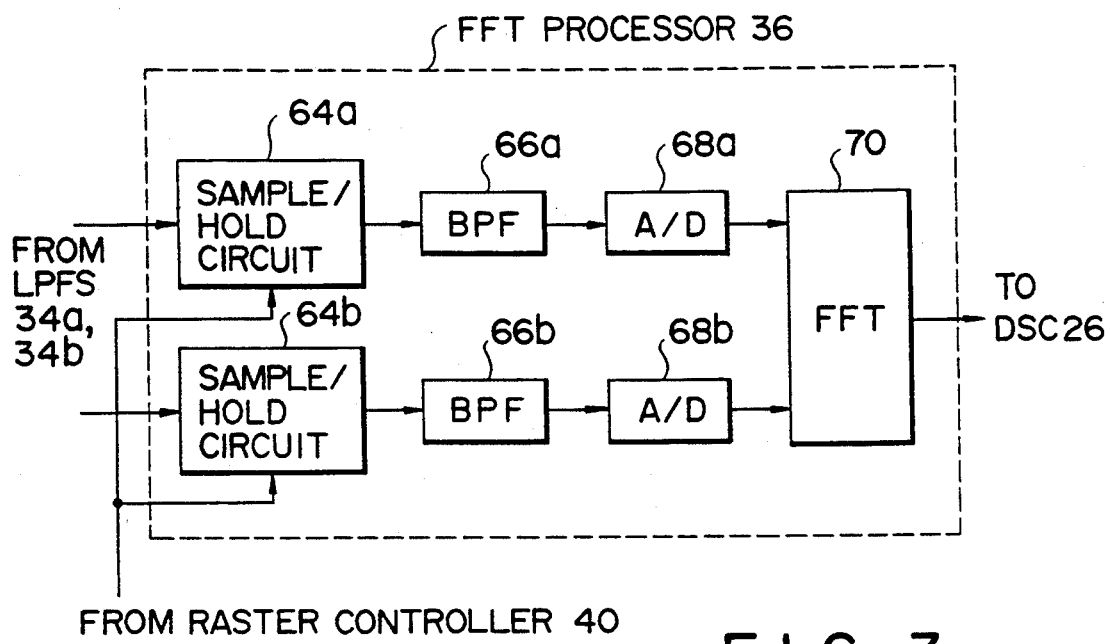
FIG. 3 is a detailed block diagram of the FFT processor of FIG. 1.
Figure 4:
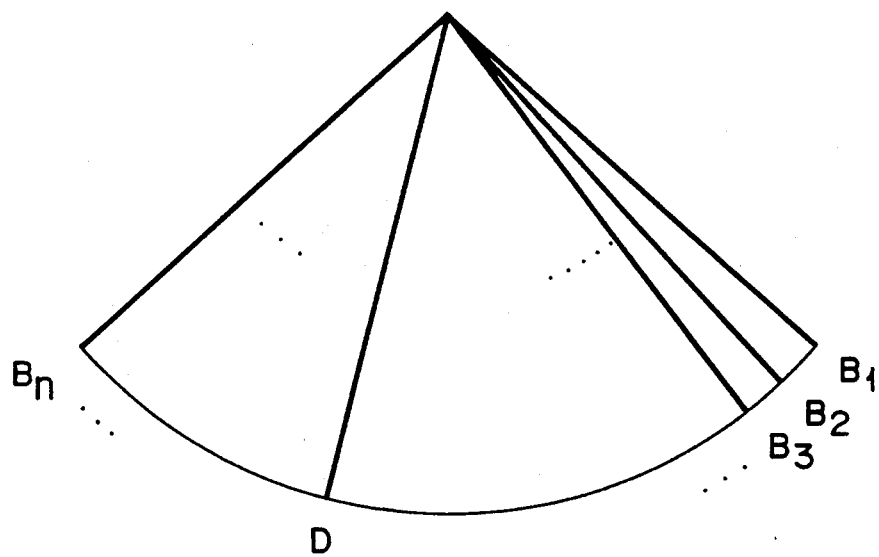
FIG. 4 is a diagram illustrating ultrasonic raster directions for explaining the operation of the first embodiment.

FIG. 3 is a detailed block diagram of FFT processor 36. Output signals of LPFs 34a and 34b are applied to fast Fourier transformer (FFT) 70 via sample/hold circuits 64a and 64b, bandpass filters (BPFs) 66a and 66b, and A/D converters 68a and 68b. FFT 70 calculates variations in a reflected signal from one point in the B-mode tomography image within a time length (data length Tw) and to obtain a blood flow pattern indicating the time-varying flow. The output of FFT 70 is coupled to DSC 26. The output of raster controller 40 is coupled to sample/hold circuits 64a and 64b to control their timing of sampling.

Figure 5:
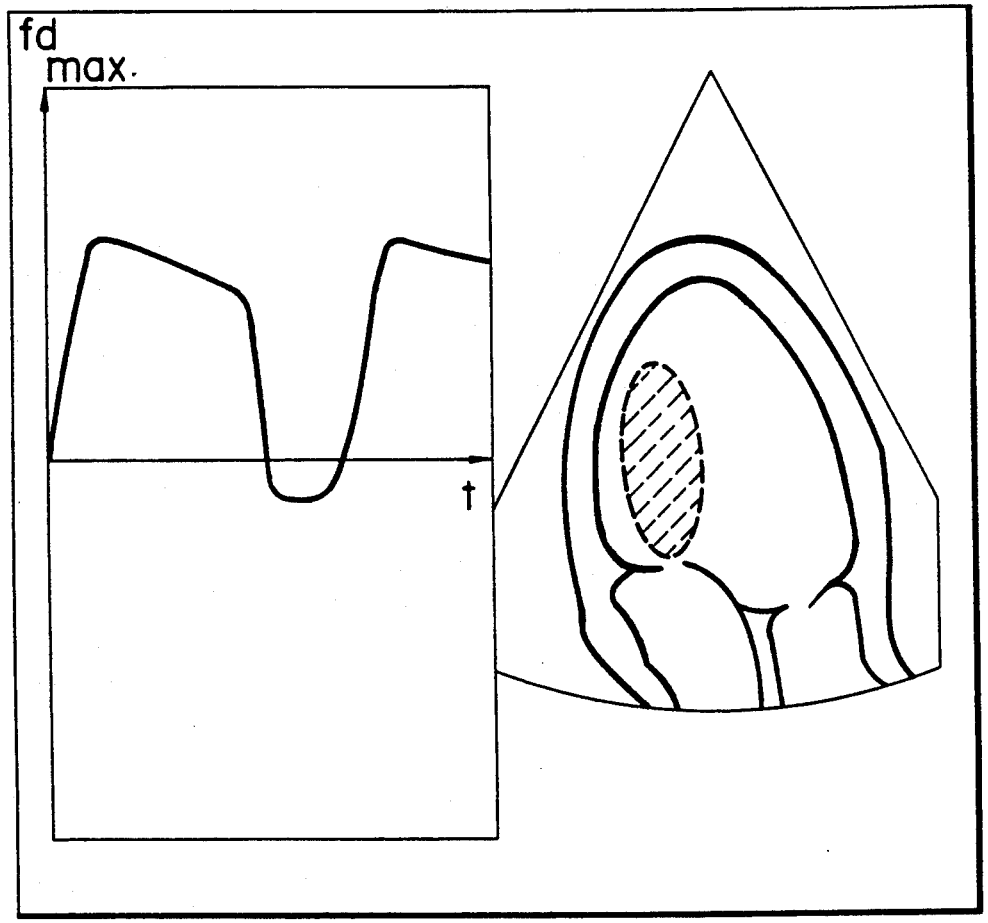
FIG. 5 illustrates a display example of the first embodiment.

Next, the operation of the first embodiment will be described. In the first embodiment, a BDF image in which the blood flow in a monochromatic B-mode tomography image is displayed in colors is obtained for a sector ranged from raster (direction of transmission of an ultrasonic wave) $B_1$ to raster $B_n$ at intervals of a fixed angle. It is assumed here that an observation point at which the frequency spectrum analysis by FF is desired is located on a raster D. The embodiment is featured by transmitting the ultrasonic wave to the raster direction for the BDF image and the raster direction for the FFT analysis in an alternate manner in order to obtain a BDF image and a blood flow pattern waveform at substantially the same time. To obtain a BDF image, it is required that an ultrasonic wave be transmitted a predetermined number of times, e.g., eight times in each of rasters and the rasters be scanned from $B_1$ to $B_n$. To this end, in the first embodiment, raster control circuit 40 supplies delay circuit 16 with control signals for switching the rasters as $B_1$, D, $B_1$, D, ... $B_1$ (the eighth scan), D, $B_2$, ... and controls the timing of sampling of data in FFT processor 36 and MTI processor 38 according to the raster direction so that only a reflected signal in a desired raster may be applied to FFT processor 36 and MTI processor 38. Thereby, a BDF image (only the blood flow is displayed in colors and the others are displayed in monochrome) and a blood flow pattern waveform indicating variations in flow velocity with time are displayed side by side on display 46 as shown in FIG. 5. The order of raster scanning in the first embodiment is illustrated in BDF/FFT mode 1 of FIG. 6.

Next, the characteristics of the first embodiment will be considered. In general, in FFT processor 36 and MTI processor 38, the repetition frequency (rate frequency) fr of ultrasonic waves is a sampling frequency. Thus, by the sampling theorem the detectable Doppler shifted frequency fd is restricted as follows.

$$fd \leq fr/2 \quad (1)$$

Thus, the upper limit $V_{max}$ of the measurable velocity is given as follows.

$$V_{max} = C \times fr/(4 \cos\theta \times fo) \quad (2)$$

where C represents the sound velocity, fo is the frequency of transmitted ultrasonic waves and $\theta$ is an angle made by the blood flow and a transmitted direction of ultrasonic wave. Thus, the blood flow pattern will be decreased by fr for the flow velocity above $+fr/2$, thus producing the so-called aliasing. In MTI processor 38 the lower limit of the measurable flow velocity is determined by the length of data applied thereto. Assuming that Tw is the length of data applied to MTI processor 38 and the number of items of data (the number of times of transmission of ultrasonic waves in the same direction) is n, the lower limit $fd_{min}$ of the detectable frequencies is given by $$fd_{min} = 1/Tw = fr/n \quad (3)$$

$$\therefore V_{min} = C \times fr/(2 \times n \times \cos\theta \times fo) \quad (4)$$

The flow velocity below the lower limit will not be colored in the BDF image. Thus, places where the flow velocity is low, such as vicinities of blood vessel walls, are apt to become blanks with no color. This will degrade the resolution of the BDF image.

In the first embodiment, since the ultrasonic wave is once transmitted to the raster D for the FFT after the ultrasonic wave is once transmitted to the raster for the BDF, the repetition frequency of the ultrasonic waves for the BDF raster will be halved as compared with the case for BDF only. Thus, it will be understood from equation (3) that the detectable lowest flow velocity $fd_{min}$ in BDF is improved by a factor of two ($\pm fr/16$) as compared with $\pm fr/8$ in the case of BDF only ($B_1$, $B_1$, ... $B_1$ (the eighth transmission), $B_2$, ...). Also, as can be seen from equation (1), $fd_{max}$ in BDF and $fd_{max}$ in FFT both relating to aliasing velocity are $\pm fr/4$, which are decreased by a factor of two as compared with $\pm fr/2$ in the case of BDF only. However, according to this embodiment, the position of the blood flow can be identified on the BDF image, a range gate of FFT (the timing of sampling in sample/hold circuits 64a and 64b) can set in that position and the blood flow pattern waveform can be displayed side by side with the BDF image. Therefore, the abnormalities of the blood flow, such as regurgitation, stricture and shunt blood flow, can be observed in real time by the use of the BDF image and the decision whether the blood flow is in an artery or in a vein or detailed blood flow inspection such as detection of the absolute value of the blood flow velocity or the extent of stricture can be made. Further, since $fd_{min}$ is improved by a factor of two as compared with the case of BDF only, if the rate frequency of the ultrasonic waves is doubled, two images will be displayed simultaneously while keeping $fd_{min}$ and $fd_{max}$ having values in the case of BDF only, that is, without degrading each of the images.

The other embodiments of the present invention will be described below. To increase the detectable lowest flow velocity $fd_{min}$ in BDF, the repetition frequency fr for the respective BDF rasters has only to be decreased. Japanese Patent Disclosure (KOKAI) No. 64-43237 (corresponding to U.S. patent application No. 423,713) discloses that two BDF rasters are repeated, namely, such that $B_1$, $B_2$, $B_1$, .... This will halve the apparent repetition frequency fr for each BDF raster, improving $fd_{min}$ in BDF by a factor of two. By utilizing this technique, for transmission of ultrasonic waves the raster order may be switched such that $B_1$, D, $B_2$, D, ... $B_1$ (the eighth transmission), D, $B_2$ (the eighth transmission), $B_3$, D, $B_4$, ... as depicted in the BDF/FFT mode 2 of FIG. 6. In this case, with $fd_{max}$ in FFT kept at $\pm fr/4$ and $fd_{max}$ in BDF becoming $\pm fr/8$, $fd_{min}$ in BDF can be improved by a factor of two as compared with that in the BDF/FFT mode 1, that is, $\pm fr/32$. Furthermore, if the number of rasters to be repeated (two in the previous case) is set at three, that is, the rasters are scanned such that $B_1$, D, $B_2$, D, $B_3$, D, ... $B_1$ (the eighth transmission), D, $B_2$ (the eighth transmission), D, $B_3$ (the eighth transmission), D, $B_4$, D, $B_5$, D, $B_6$, D, $B_4$, ... as depicted in the BDF/FFT mode 3 of FIG. 6, then $fd_{min}$ in BDF becomes $\pm fr/48$, which is improved by a factor of three as compared with the BDF/FFT mode 1 with $fd_{max}$ in FFT kept at $\pm fr/4$.

As described above, since the raster for BDF is repeated in units of several rasters and the FFT raster is interposed between two BDF rasters, the aliasing frequency $fd_{max}$ in a blood flow pattern is kept at $\pm fr/4$.

Therefore, the more the number of repeating BDF rasters, the lower is the flow velocity that can be detected and displayed in a BDF image. That is, even the flow velocity in the vicinities of blood vessel walls can be displayed. A high-resolution blood flow image can be displayed without any blank portion in a blood flow image. In other words, narrow blood walls can be detected easily.

In the above embodiment, the FFT raster is interposed between two BDF rasters. Alternatively, the FFT raster may be interposed after an end of one repetition cycle ... or $B_1$, $B_2$, $B_3$, D, $B_1$, $B_2$, $B_3$, D, .... These scans are illustrated as BDF/FFT mode $2a$ and BDF/FFT mode $3a$ in FIG. 6.

Although the preferred embodiments of the present invention have been disclosed and described, it is apparent to those skilled in the art that various embodiments and modifications are possible. For example, the number of rasters for a BDF image to be repeated is not limited to two or three, but may be more than three.

According to the present invention, as described above, by transmitting the ultrasonic waves to the BDF raster and to the FFT raster alternately, the BDF image and the blood flow pattern can be obtained simultaneously. As a result, FFT range gates can be set to obtain a blood flow pattern while the position and direction of a blood vessel wall is observed in real time on the BDF image, thus shortening the operation time and lightening operator's burden. In addition, by changing the BDF raster repeatedly in units of several rasters in place of repeating the BDF raster in several times, the low flow velocity detecting capability of a BDF image can be improved without degrading the aliasing velocity in FFT. Consequently narrow blood vessel walls can be detected easily and moreover the aliasing will not occur.

Additional advantages and modifications will readily occur to those skilled in the art. Therefore, the invention in its broader aspects is not limited to the specific details, representative devices, and illustrated examples shown and described herein.

Accordingly, various modifications may be made without departing from the spirit or scope of the general inventive concept as defined by the appended claims and their equivalents.

What is claimed is:

1. An ultrasonic diagnostic apparatus comprising:

means for scanning ultrasonic waves in a section of an object under examination;

means for detecting the intensity of reflected ultrasonic waves from the object to obtain a tomography image;

means for detecting Doppler shifts of the reflected ultrasonic waves;

means for displaying blood flow in colors in the tomography image obtained by said intensity detecting means according to the Doppler shifts detected by the detecting means;

means for analyzing a frequency spectrum of the Doppler shifts of the reflected ultrasonic waves from a given point in the tomography image; and transmission direction control means for setting a transmission direction of the ultrasonic waves to one of the direction required for displaying the blood flow in colors and the direction required for analyzing the frequency spectrum in a predetermined order.

2. An apparatus according to claim 1, in which said transmission direction control means comprises means for alternately setting the transmission direction of the ultrasonic waves to the direction required for displaying the blood flow in colors and the direction required for the frequency spectrum at each transmission of the ultrasonic waves.

3. An apparatus according to claim 2, in which said transmission direction control means comprises means for sequentially varying the transmission direction required for displaying the blood flow in colors while transmitting the ultrasonic waves i (a positive integer) times in the same direction.

4. An apparatus according to claim 2, in which said transmission direction control means comprises means for repeatedly varying the transmission direction required for displaying the blood flow in colors from a first direction to a second direction while transmitting the ultrasonic waves once in each of directions.

5. An apparatus according to claim 1, in which said transmission direction control means comprises means for repeatedly varying the transmission direction required for displaying the blood flow in colors from a first direction to a second direction while transmitting the ultrasonic waves once in each of directions and for setting the transmission direction required for analyzing the frequency spectrum once in each cycle of repetition of varying the transmission direction.

6. An apparatus according to claim 1, further comprising means for displaying the tomography image in which blood flow is displayed in colors and a pattern of time-varying flow velocity indicating the result of the analysis of the frequency spectrum side by side.

7. A method of driving an ultrasonic diagnostic apparatus having a Doppler flow mapping mode for displaying blood flow in colors in a tomography image and a frequency analyzing mode for displaying a blood flow pattern indicating a time-varying blood flow velocity at a given point in the tomography image, comprising the steps of:

transmitting ultrasonic waves to scan a section of an object under examination so that the ultrasonic wave is transmitted to a given raster direction for the frequency analyzing mode each time the ultrasonic waves are transmitted a predetermined number of times for the Doppler flow mapping mode;

brightness modulating the intensity of reflected ultrasonic waves to obtain a tomography image of the section of the object;

detecting Doppler shifts in the reflected ultrasonic waves to obtain a Doppler shift signal;

sampling the Doppler shift signal in synchronism with the transmission of the ultrasonic waves for the Doppler flow mapping mode, calculating the mean velocity, variance and power from the sampled signal, and displaying the results of the three calculations in colors in the tomography image; and sampling the Doppler shift signal in synchronism with the transmission of the ultrasonic waves for the frequency analyzing mode, analyzing the frequency spectrum of the sampled signal, and displaying a pattern of time-varying flow velocity.

8. A method according to claim 7, in which the step of transmitting the ultrasonic waves comprises a substep of transmitting ultrasonic waves alternately in the direction of transmission for the Doppler mapping mode and in the given direction of the transmission for the frequency analyzing mode.

9. A method according to claim 8, in which the step of transmitting the ultrasonic waves comprises a substep of varying the direction of transmission of ultrasonic waves in the Doppler flow mapping mode while transmitting the ultrasonic waves i (an positive integer) times in the same direction.

10. A method according to claim 9, in which the step of transmitting ultrasonic waves comprises a substep of sequentially varying the directions of transmission of ultrasonic waves in the Doppler flow mapping mode while transmitting ultrasonic waves once in each of directions from a first direction to a second direction, making transmission of ultrasonic wave in the first direction again after the transmission in the second direction and performing this repetition i (an positive integer) times.

11. A method according to claim 7, in which the step of transmitting of ultrasonic waves comprises a substep of sequentially varying the directions of transmission of ultrasonic waves in the Doppler flow mapping mode while transmitting ultrasonic waves once in each of directions from a first direction to a second direction, making transmission of ultrasonic waves in the first direction again after the transmission in the second direction, performing this repetition i (an positive integer) times, and transmitting ultrasonic waves in a given direction for the frequency analyzing mode with each cycle of the repetitive transmission from the first direction to the second direction.

* * * * *